United States Patent [19]

Stock

[11] Patent Number: 5,052,213
[45] Date of Patent: Oct. 1, 1991

[54] EXHALATION AIR ANALYSIS DEVICE

[75] Inventor: Burghard Stock, Lübeck, Fed. Rep. of Germany

[73] Assignee: Drägerwerk Aktiengesellschaft, Lübeck, Fed. Rep. of Germany

[21] Appl. No.: 336,469

[22] Filed: Apr. 12, 1989

[30] Foreign Application Priority Data

Apr. 14, 1988 [DE] Fed. Rep. of Germany ....... 3812235

[51] Int. Cl.$^5$ ............................................. G01N 27/62
[52] U.S. Cl. ....................................... 73/23.3; 422/84
[58] Field of Search .................. 73/863.86, 864.81, 23; 422/84

[56] References Cited

U.S. PATENT DOCUMENTS

| 3,338,087 | 8/1967 | Moberg et al. | 73/23 |
| 3,362,228 | 1/1968 | Stuben | 73/23 |
| 4,362,635 | 12/1982 | Hutson | 422/84 |

FOREIGN PATENT DOCUMENTS

| 1408282 | 7/1988 | U.S.S.R. | 73/23 |
| 892348 | 3/1962 | United Kingdom | 73/23 |

Primary Examiner—Hezron E. Williams
Assistant Examiner—Craig Miller
Attorney, Agent, or Firm—McGlew & Tuttle

[57] ABSTRACT

An exhalation air analysis device, in particular for alcohol analysis including a flow duct coming from the tested person to a testing housing having a movable duct element with a recess. The duct element can be adjusted in two different settings in the housing. In the first position the recess is connected to an inlet and outlet of the exhalation air line, so that the recess forms a part of the flow duct of the exhalation air. In a second position of the duct element, its recess is cut off from the flow duct and connected to a detector. The volume of the recess forms a part of the analysis chamber required for the analysis.

10 Claims, 3 Drawing Sheets

EXHALATION AIR ANALYSIS DEVICE

BACKGROUND OF THE INVENTION

Field of the Invention

The invention relates, in general, to gas analyzers and, in particular, to a new and useful exhalation air analysis device with a flow duct, through which the exhalation air of a tested person flows and with an analysis chamber in which the exhalation air has contact with a detector reacting to a component of the exhalation air and generating a metering signal.

For the analysis of human exhalation air, and in particular for the determination of the alcohol concentration in the exhalation air, analysis devices have been used for many years in addition to the known chemically operating test tubes, which use a detector reacting specifically to the concentration of the respective substance and generating a respective electrical output signal. Electro-chemical detectors are used in particular. Herein especially those detectors working on the basis of the coulometric metering principle have proven successful for alcohol analysis.

In such a metering process the concentration is not determined directly, but the amount of a species or substance which is transformed on the detector surface in a certain period of time. It is also called an absorption, process. The invention is related specifically to the use of detectors working according to the coulometric process or another absorption process.

In order to determine the concentration of the substance in the exhalation air by means of the amount metered, it is necessary to isolate a defined volume of the exhalation air for testing. For this purpose the respective analysis devices have therefore an analysis chamber, which is usually connected to the flow duct through which the ventilation air of the test person flows.

U.S. Pat. No. 3,854,320 describes a ventilation air analysis device, in which the analysis chamber is a part of the flow duct which is arranged permanently in the path of the ventilation air. The detector is arranged in the analysis chamber, but it is at first covered by a cap during the breathing process. Only toward the end of the breathing process is the exhalation air flow interrupted and the detector uncovered by the lifting of the cap, so that the metering or measuring can take place.

In the analysis device described in German patent No. A-29-44 444 the analysis chamber is connected to the flow duct by means of a connecting line. At the desired moment a sample is sucked from the flow duct into the analysis chamber. For this purpose a pumping device connected to the analysis chamber comprising an element which moves in a piston-like manner in a respective housing, is provided.

SUMMARY OF THE INVENTION

In order to provide an exhalation air analysis device with a simplified design, reliable operation and an exactly defined analysis chamber volume, the invention includes a flow duct which encloses a duct element with a recess. The duct element has an inlet and an outlet for the exhalation air and is adjustable to at least two settings; a first setting in which the recess is connected with the inlet and the outlet for the exhalation air and the recess forms a part of the flow duct, and a second setting in which the recess is disconnected from the flow duct and connected to the detector and the recess forms at least a part of the analysis chamber.

While the movable duct element is in the first position, the test person meets little flow resistance when exhaling.

In comparison with the known device according to U.S. Pat. No. 3,854,320 it is advantageous that the volume of the flow duct including the section formed by the recess of the duct element is relatively small.

The recess is flushed by means of the test person's exhalation air. It is advantageous for the velocity and accuracy of the metering if the volume of the analysis chamber which is not flushed is relatively small, i.e. the recess should represent a substantial part of the total volume of the analysis chamber (at least 70%, preferably at least 80%). Preferably the ratio of the volume of the recess to the volume of the analysis chamber can also be adjusted to the desired exhalation air diluting ratio if a sensitive detector has to analyze a relatively high concentration.

Toward the end of the exhaling process the movable duct element is moved from the first position into the second position. The moment of the switching is determined by known means not a subject of the present invention. The volume to which the analysis refers is definitely determined by the fact that in the second position the recess is connected to the analysis chamber only.

Preferably the arrangement of the detector in the housing, the arrangement of the duct element in the second position and the recess of the duct element are coordinated so that in the second position the detector is positioned directly adjacent to the recess. By this means the analysis chamber is practically formed by the recess of the duct element. This leads to an increase in the metering accuracy and metering velocity, as long as diffusion paths between the recess of the duct element and the detector are avoided.

Accordingly, it is an object of the invention to provide an exhalation air analysis device which is used for testing exhalation air of a person connected to an exhalation air line and which comprises a housing having an inlet connection to the inhalation air line and an outlet connection connected back to the exhalation line and being spaced away from the inlet connection and which also includes a test detector line space from the inlet and the outlet which is connected to a test detector, the device also including a duct element which is movable in the housing relative to the inlet and the outlet and the detector line and has a recess which defines a connecting flow passage which may be selectively positionable between the inlet and the outlet to interconnect them or between the inlet and the test detector line so as to connect the inlet to the detector line and provide a gas analysis volume with the test detector line.

A further object of the invention is to provide an exhalation gas analyzer which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

DETAILED DESCRIPTION OF THE DRAWINGS

Figure 1:
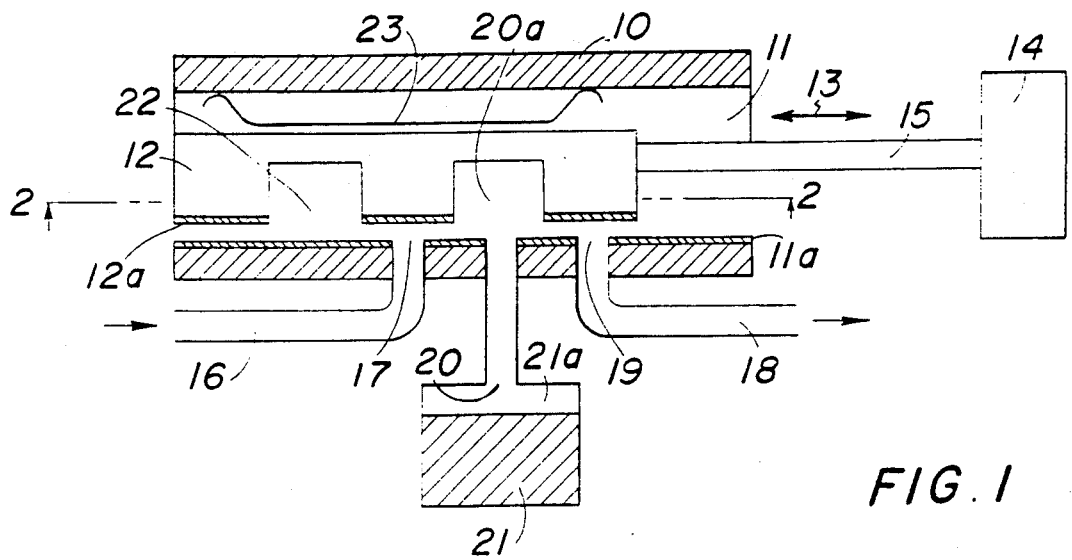
FIG. 1 is a longitudinal section through a part of an exhalation air analysis device of a first embodiment.
Figure 2:
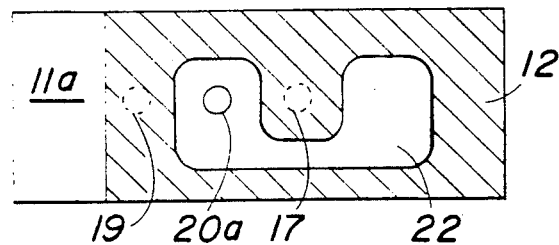
FIG. 2 and 3 are a sectional views taken along the line II—II of FIG. 1 in two different positions of the duct element.
Figure 3:
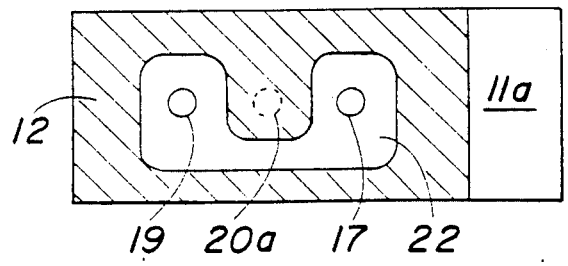

Referring to the drawings, in particular, the invention embodied therein in FIGS. 1-3 comprises an apparatus for testing exhalation air of a person who is connected to an exhalation air line 16 and including a housing 10 having an inlet 17 for the exhalation air. The housing 10 also includes an outlet 19 spaced from the inlet 17 as well as an opening 20a which is spaced from each of the inlet and the outlet and is connected in a detector line 20 to a detector 21. In accordance with the invention, a slide 12 is movable in the housing 10 between a position in which the inlet 17 is connected to the outlet 19 through a recess 22. The recess 22 defines a connecting flow passage which is selectively positionable between the inlet 17 and the outlet 19 either to interconnect the inlet to the outlet or it may be positioned between the inlet and the test detector line 20 to interconnect the inlet to the test detector line. In the embodiment of FIGS. 1, 2, and 3, the slide 12 is movable to effect communication of the exhalation air with a detector 21 by connecting the detector line 20 to the inlet 16 by proper positioning of the slide 12. A feature of the construction of the invention is that the recess 22 forms a portion of the volume which is exposed to the detector 21 so that it is assured that a sufficient amount of exhalation air is being detected and this connection may be effected very quickly.

The FIGS. 1 to 3 show a part of a exhalation air analysis device for the taking of a sample and its analysis.

The housing 10 has an approximately rectangular housing recess or cavity 11 in which a duct element having the shape of a slider 12 can be moved into at least two positions, as is indicated by the double arrow 13. The movement is effected by means of an element actuation 14 on a connecting rod 15 represented symbolically.

The ventilation air supply to the test person is through a supply line 16 by means of a mouth piece (not shown). Supply line 16 opens into an inlet 17 in the housing wall. For the disposal of the exhalation air a disposal or discharge line 18 is provided which is connected to an outlet 19 in the housing wall.

The opening 20a of a connecting duct 20 to a detector 21, is situated between the inlet 17 and the outlet 19.

The slider 12 has a recess 22. In a first position of the slider shown in FIG. 3 the recess 22 is aligned with the inlet 17 and the outlet 19 of the supply line 16 and the disposal line 18 and therefore it forms a part of a flow duct 16, 22, and 18 for the exhalation air. At the same time the connecting duct 20 is blocked. In order to achieve a reliable sealing, silicium sealing rings 12a and 11a are arranged on the sealing surfaces of the slider 12 and the housing recess 11 facing one another, and the slider as a whole is pressed against the sealing surfaces by a spring 23.

At an appropriate moment toward the end of the exhaling phase the slider 12 is moved into a second position shown in FIG. 1 and 2, in which its recess 22 is aligned with the opening 20a of the connection duct 20, while the inlet 17 and the outlet 19 are blocked. Now the exhalation air sample in the recess 22 can reach the detector, where a metering signal is generated. In this position the recess 22, the connecting duct 20 and the gas chamber 21a of the detector 21 form an analysis chamber with a defined volume, so that an exact metering, in particular with a coulometric detector is possible.

In the shown embodiment the supply line is closed when the duct element is switched from the first position to the second position. Therefore, the test person can no longer breathe adequately. If this temporary condition is not desired, a second flow duct (not shown) for the exhalation air is provided, which is either constantly opened as a permanent bypass or opened when the duct element is switched to the second position.

Figure 4:
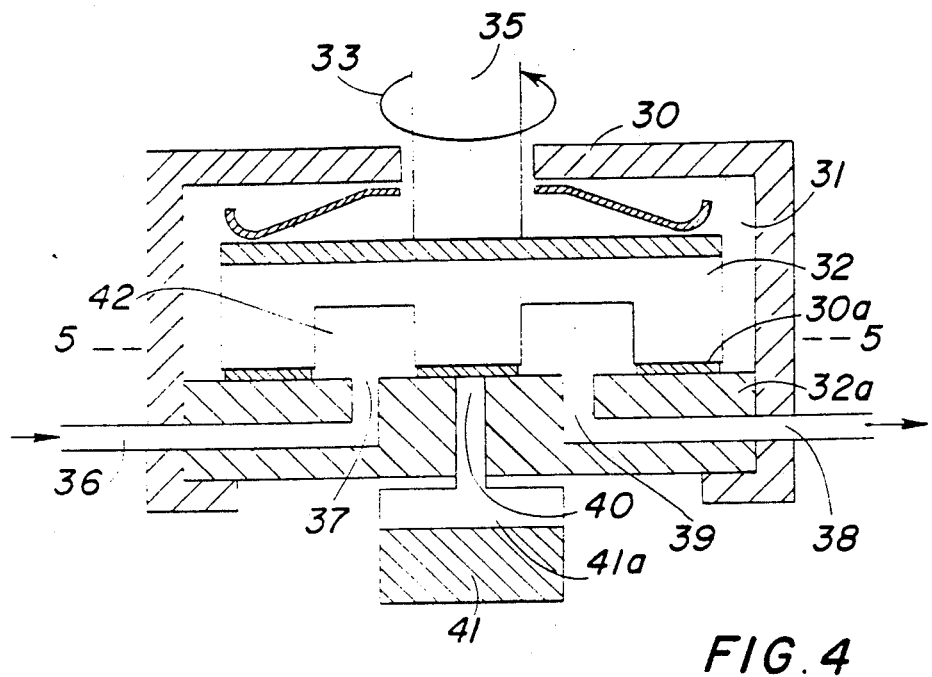
FIG. 4 is a sectional view through a part of a second embodiment of the invention taken along the line IV—IV of FIG. 5.
Figure 5:
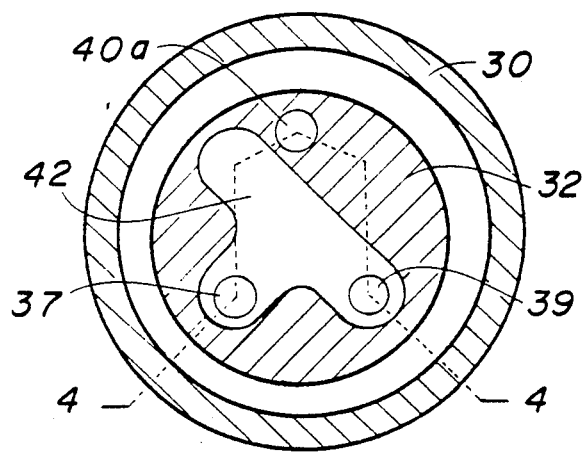
FIG. 5 and 6 are sectional views taken along the line V—V in FIG. 4 in two different positions of the duct element.
Figure 6:
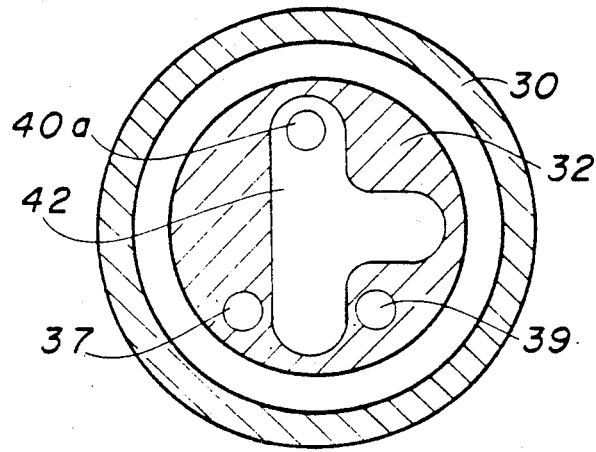

The embodiment according to FIG. 4 to 6 is similar to the one in FIG. 1 to 3, only that here a cylindrical duct element 32 is used instead of the slider. The cylindrical duct element 32 is rotatable in an also cylindrical recess 31 of the housing 30 on an axle 35 rotatably mounted in the housing 30 in the direction of rotation shown by the arrow 33.

Here, too, the form of the recess 42 and the positioning of the inlet 37 of the supply line 36 and the outlet 39 of the disposal line 38 and the opening 40a of the connection duct 40 leading to the detector 41 are coordinated so that in a first position (shown in FIG. 4 and 5) the recess 42 is aligned with the inlet 37 and the outlet 39, while the testing opening 40a of the flow duct or connection line 40 to the detector 41 is cut off by the cylindrical duct element 32. The sealing can be guaranteed advantageously if the duct element 32 or at least the sealing surface 30a and/or the corresponding counter-surface 32a of the housing 30 are made from graphite. In the represented first position the recess 42 also forms a part of the flow duct 40.

In the position represented in FIG. 6 in contrast, the recess 42 is aligned with the opening 40a, while the inlet 37 and the outlet 39 are blocked by the cylindrical duct element 32. Therefore the recess 42 is again a part of the analysis chamber.

Figure 7:
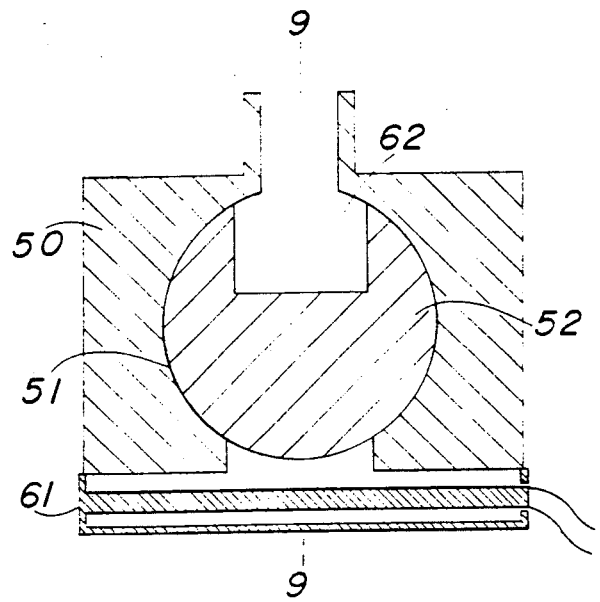
FIG. 7 and 8 are sectional views through a part of a third embodiment of the invention along a line VII—VII in FIG. 9 in two different positions of the duct element.
Figure 8:
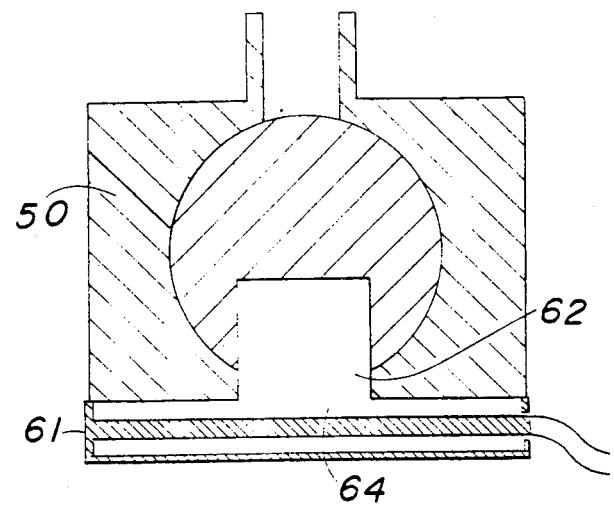
Figure 9:
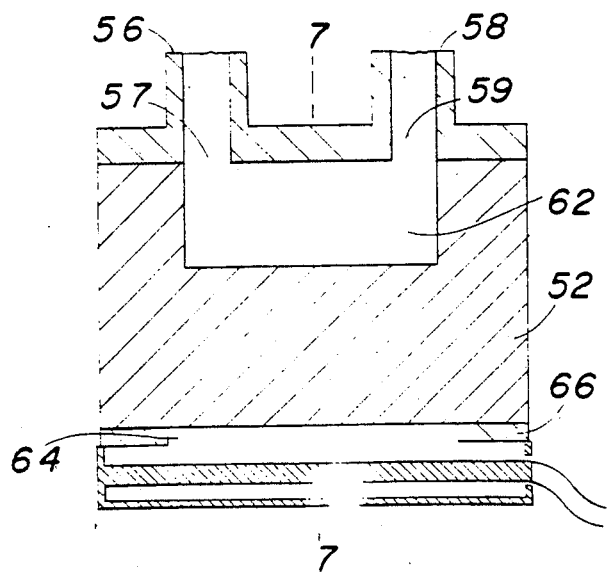
FIG. 9 is a section taken along the line IX—IX of FIG. 7.

In the embodiment according to the FIG. 7 to 9 a cylindrical duct element 52 rotatable around its cylinder-axis is used. The housing 50 has a respective cylindrical housing cavity or recess 51. In this embodiment the recess 62 of the duct element 52 is opened toward its cylinder jacket, and the opening in the cylinder jacket surface is relatively large, preferably about as large as the operating surface of detector 61.

In the first position (shown in FIG. 7 and 9) the recess 62 of the duct element 52 is aligned with the inlet 57 and the outlet 59 of the supply line 56 and the disposal line 58, of which only the connecting flanges are shown.

In the second position (FIG. 8) of the duct element 52 the recess 62 faces the detector 61 directly. The opening 64 in the wall of the housing 50 is approximately as large as the opening of the recess 62 in the cylinder jacket of the duct element 52. By this means the volume of the analysis chamber is practically only formed by the recess 62 and the small volume of the opening 64. Long diffusion paths are avoided, so that a speedy metering and measuring is possible.

The cylindrical duct element 52 is received in the housing 50 by a fitting guide, so that no gas can escape to the detector 61 during the flushing and the duct element 52 is still easily rotatable. The detector 61, which can be exchanged, is arranged in a receiving groove 66 of the housing 50 with its operating surface positioned opposite the opening 64.

Preferably the housing is heated to 34° C. at least in order to avoid a condensation of the steam in the exhalation air.

While specific embodiments of the invention have been shown and described in detail to illustrate the application of the principles of the invention, it will be understood that the invention may be embodied otherwise without departing from such principles.

What is claimed is:

1. An apparatus for testing exhalation air of a person who is connected to an exhalation air line, comprising a housing having an inlet connection to the exhalation air line, an outlet in said housing spaced from said inlet connected to the exhalation air line, a gas test detector line in said housing spaced from said inlet and outlet, a gas test detector in said gas test detector line, and a duct element movable in said housing relative to said inlet, said outlet and said gas test detector line and having a recess defining a connecting flow passage which is selectively positionable upon movement of said duct element relative to said inlet, said outlet and said gas test detector line to selectively position said connecting flow passage between said inlet and said outlet to interconnect said inlet and said outlet and to selectively position said connecting flow passage in communication with said gas test detector line, said connecting flow passage forming a gas analysis volume with said gas test detector line.

2. An exhalation air analysis device according to claim 1, wherein said duct element is adjustable between at least two positions in said housing including a first position in which the recess of said duct element is connected to said inlet and said outlet for the exhalation air and in which the recess forms a part of a continuing flow path with said exhalation air line and a second position in which the recess of said duct element is cut off from its connection to said outlet and said inlet and is connected to said gas test detector line, said recess forming at least a part of an analysis chamber which is defined by said gas test detector line and said recess, said recess being such as to overlie said gas test detector line in said second position.

3. An apparatus according to claim 1, wherein said gas test detector line has a gas test detector line volume and said recess has a recess volume, said recess volume comprising a large portion of said gas analysis volume than said gas test detector volume.

4. An apparatus according to claim 1, wherein said gas test detector line has a gas test detector line volume and said recess has a recess volume the ratio of the recess volume to the gas analysis volume corresponds to a desired exhalation gas dilution ratio.

5. An apparatus according to claim 1, wherein said duct element comprises a slider being slidable in said housing and including means biasing said slider in a direction in which it overlies the opening of said inlet and said outlet and said gas test detector line.

6. An apparatus according to claim 1, wherein said duct element comprises a rotatable member of cylindrical shape rotatably mounted in said housing, said inlet, said outlet and said gas test detector line being circumferentially spaced and said recess having radially extending passages disposed at an angle from each other.

7. An apparatus according to claim 1, wherein said duct element is cylindrical and has a recess opening radially outwardly to its circumference, said housing having a wall opening into a space in which said duct element is rotatable and which defines an inlet to the gas test detector line and said gas test detector being positioned in alignment with the opening.

8. An apparatus according to claim 1, wherein each of said inlet, outlet and gas test detector lines have openings in said housing arranged around a central axis, and said duct element is rotatable in said housing in a position overlying the openings of said inlet, said outlet and said gas detection line and having said recess on its face which effectively connects together said inlet and said outlet and alternatively connects with said gas detection line forming a gas analysis volume with said gas test detector line.

9. An apparatus for the gas detection of exhalation gases according to claim 1, wherein said housing has a cylindrical chamber, said gas chamber line is connected radially into said cylindrical chamber, said duct element including positioned in said cylindrical chamber, said rotatable duct member including said recess, said recess extending outwardly to its circumference to communicate selectively with said inlet and said outlet so that said inlet is connected to said outlet and to a rotated position communicating with said gas detection line forming the gas analysis volume with said gas detection line.

10. An apparatus for analyzing exhalation air comprising a housing having an exhalation air inlet extending into said housing, a gas detector line connected into said housing, a gas detector in said gas detector line, a disposal line connected into said housing, said housing having an interior chamber overlying the connection of said inlet, said gas detection line and said disposal line, a slider slidable in said housing and having a side facing each of said air inlet line, said gas detection line and said disposal line connected into said housing, means connected to said slider for moving it backwardly and forwardly in said housing, said slider having a recess in the surface overlying the respective said inlet said gas detector line and said disposal line connected into said housing, means biasing said slider into engagement with said housing, said slider having a recess which may be positioned in at least two positions of said slider to selectively connect said recess with said gas detector line and to interconnect said inlet with said outlet through said recess.

* * * * *